(12) United States Patent
Konrad et al.

(10) Patent No.: US 6,361,995 B1
(45) Date of Patent: Mar. 26, 2002

(54) PROTECTION OF PANCREATIC β-CELLS DURING ISLET ISOLATION AND ASSESSMENT OF ISLET VIABILITY AND CANDIDATE DIABETES DRUGS AFTER ISLET ISOLATION

(75) Inventors: Robert Konrad, Hoover; Jeffrey Kudlow, Birmingham, both of AL (US)

(73) Assignee: NAB Research Foundation, Birmingham, AL (US)

( * ) Notice: Subject to any disclaimer, the term of this patent is extended or adjusted under 35 U.S.C. 154(b) by 0 days.

(21) Appl. No.: 09/625,869

(22) Filed: Jul. 26, 2000

Related U.S. Application Data

(60) Provisional application No. 60/145,582, filed on Jul. 26, 1999.

(51) Int. Cl.[7] .................................................. C12N 5/00
(52) U.S. Cl. ...................... 435/325; 435/366; 435/374; 435/375
(58) Field of Search .......................... 435/29, 325, 366, 435/374, 375

(56) References Cited

FOREIGN PATENT DOCUMENTS

WO    WO 98/09637    * 12/1998

OTHER PUBLICATIONS

Konrad, R., et al. Glucose and Streptozotocin Stimulate p135 O–Glycosylation in Pancratic Islets. *Biochemical and Biophysical Research Communication vol. 263*, 2000, pp.26–32.

Cardinal, J., et al. Differential Metabolite Accumulation May be the Cause of Strain Differneces in Sensitivity to Streptozotocin–Induced β Cell Death in Inbred Mice*. *Endocrinology vol. 139*, No. 6, 1998, pp. 2885–2891.

Kröncke, K–D., et al. Nitric Oxide Generation Doring Cellular Metabolization of the Diabetogenic N–Methyl–N–Nitroso–Urea Streptozotozin Contributes to Islet Cell DNA Damage. *Biol. Chem. Hoppe–Seyler vol. 376*, Mar. 19995, pp. 179–185.

Kaneto, H., et al. Apoptic Cell Death Trigered by Nitric Oxide in Pancreatic β–Cells. *Diabetes vol. 44*, Jul. 1995, pp. 733–738.

* cited by examiner

*Primary Examiner*—Christopher R. Tate
*Assistant Examiner*—Randall Winston
(74) *Attorney, Agent, or Firm*—Benjamin Aaron Adler

(57) ABSTRACT

Standard pancreatic islet isolation results in β-cell toxicity due to nitric oxide and/or streptozotocin-like molecules that are generated during the isolation process. This toxicity can be limited by the addition of compounds that work through the glucosamine pathway in islets and/or by the addition of nitric oxide inhibitors. Unless prevented, this toxicity results in β-cells being unable to properly respond to high glucose, glucosamine, N-acetylglucosamine, or streptozotocin by increasing their relative amount of O-glycosylated protein. Likewise, in order to assess islet viability or the effect of diabetes drugs on β-cell function, islets that have been adequately protected during their isolation can be stimulated with low glucose, high glucose, glucosamine, N-acetylglucosamine, or streptozotocin with or without the drug(s) of interest present. By analyzing the pattern of islet protein O-glycosylation that occurs, one can determine whether the islets are viable and whether or not the candidate drug(s) might be useful in the treatment of diabetes.

4 Claims, 12 Drawing Sheets

N-Acetylglucosamine    Streptozotocin

PROTECTION OF PANCREATIC β-CELLS DURING ISLET ISOLATION AND ASSESSMENT OF ISLET VIABILITY AND CANDIDATE DIABETES DRUGS AFTER ISLET ISOLATION

CROSS-REFERENCE TO RELATED APPLICATION

This non-provisional patent application claims benefit of provisional patent application U.S. Ser. No. 60/145,582, filed Jul. 26, 1999, now abandoned.

BACKGROUND OF THE INVENTION

1. Field of the Invention

The present invention relates generally to the fields of pancreatic islet isolation and medical therapy for diabetes. More specifically, the present invention relates to improved procedures for isolating pancreatic islets that better protect the islets during the isolation process. In order to screen for new drugs to treat type 2 diabetes, or to prepare islets for transplantation for type 1 diabetes, isolated islets must be protected from toxic molecules that form during the isolation process.

2. Description of the Related Art

Early in the course of type 2 diabetes, pancreatic β-cell function is sufficient such that in many patients, oral hypoglycemic agents are adequate to compensate for increased insulin resistance (1). As type 2 diabetes progresses, however, β-cells lose their capacity to produce sufficient amounts of insulin to control the blood glucose level and patients become increasingly hyperglycemic (2). It has been suggested that the hyperglycemia itself may cause damage to β-cells (3–5). The exact mechanism by which an increased concentration of glucose may affect β-cells, however, is not completely elucidated.

One metabolite of glucose that has been proposed to mediate adverse effects of hyperglycemia is glucosamine (2-amino-2-deoxyglucose) (6,7). Glucosamine is a product of glucose metabolism and is synthesized from fructose-6-phosphate by the apparently unique and rate limiting enzyme, glutamine:fructose-6-phosphate amidotransferase (GFAT) (8–10). This metabolic step provides the substrate UDP-N-acetylglucosamine (UDP-GlcNAc) for glycoprotein synthesis. Quantitatively, most glycosylation occurs on proteins destined for export from the cell or for the plasma membrane of the cell. In eukaryotic cells, however, there is a cytoplasmic form of glycosylation that involves O-linkage of the monosaccharide, N-acetylglucosamine (GlcNAc), to proteins at serine or threonine residues (11–19). An enzyme responsible for this form of protein modification, O-linked N-acetylglucosamine transferase (OGT), has recently been characterized, and its cDNA has been cloned (20). Studies on the tissue distribution of O-GlcNAc transferase have indicated that O-linked N-acetylglucosamine transferase mRNA, although ubiquitous, is particularly abundant in the pancreatic β-cell (21, 22).

Interestingly, an analog of N-acetylglucosamine called streptozotocin (STZ) has been used to create animal models of diabetes (27). A nitrosourea group is present at a position that corresponds to the acetate in N-acetylglucosamine (FIG. 6). A single dose of 50–100 mg/kg of streptozotocin administered to a rat causes death of most of the β-cells and development of diabetes. Very recently, streptozotocin has been shown to act by inhibiting the enzyme O-GlcNAc-selective N-acetyl-β-D-glucosaminidase (O-GlcNAcase), which cleaves O-linked N-acetylglucosamine off protein (21, 22). These data suggest why the β-cell, with its elevated level of O-GlcNAc transferase, may be particularly vulnerable to streptozotocin.

Supporting this idea is a recent report that β-cell O-linked protein glycosylation is involved in β-cell apoptosis in vivo since administration of streptozotocin to rats prior to the induction of hyperglycemia results in irreversible increases in β-cell O-glycosylation and subsequent β-cell apoptosis (23). In addition, both glucose and streptozotocin stimulate O-glycosylation of a 135 kD protein in isolated islets in vitro, although the effect did not seem as dramatic as the reported in vivo observations (24).

The prior art is deficient in the lack of effective means of blocking the formation and action of molecules that are toxic to the β-cells of the pancreatic islets when the islets are being isolated from the pancreas. The prior art is also deficient in a means by which to determine if pancreatic β-cells are traumatized by toxic molecules such as nitric oxide or streptozotocin-like compounds during the isolation process. Additionally, the prior art is deficient in a means by which to test diabetes drugs to see if they affect glucose toxicity to β-cells by acting through the O-linked protein glycosylation pathway that glucose, analogues of glucosamine, and streptozotocin affect. The present invention fulfills these long-standing needs and desires in the art.

SUMMARY OF THE INVENTION

The present invention demonstrates that during standard islet isolation (which has been performed for the last 30 years), pancreatic β-cells are affected adversely by nitric oxide and/or streptozotocin-like molecules that form during the isolation process. In order to prevent nitric oxide toxicity or streptozotocin-like toxicity to the islets during the isolation process, the islets need to be isolated in the presence of high glucose and glutamine, glucosamine, N-acetylglucosamine, or other agents that act through the N-acetylglucosamine (GlcNAc) pathway. Such toxicity can further be reduced by the addition of nitric oxide synthase (NOS) inhibitors and/or nitric oxide (NO) scavengers. The present invention also discloses that streptozotocin, glucose, and glucosamine all increase the O-glycosylation of protein in β-cells, and that assaying for modification of this protein can allow a determination to be made as to islet viability as well as which potential diabetes drugs might be likely candidates for acting through the O-linked glycosylation pathway.

Glucose, glucosamine, and streptozotocin stimulate O-glycosylation of a single 135 kD β-cell protein in isolated rat islets. The effect of glucose, but not that of glucosamine or streptozotocin was blocked by inhibition of glutamine:fructose-6-phosphate amidotransferase, suggesting that glucose acts through the glucosamine pathway to provide more UDP-N-acetylglucosamine substrate for O-linked N-acetylglucosamine transferase to attach to p135. The effect of glucose on p135 O-glycosylation was reversible while that of streptozotocin was not, indicating that streptozotocin irreversibly inactivated β-cell O-GlcNAcase. Experiments performed in clonal β-cell lines demonstrated an inability of β-cells grown in culture to regulate increased p135 O-glycosylation in response to glucose, glucosamine, or streptozotocin, indicating a fundamental difference between β-cells grown in culture and actual β-cells in islets. Together, these data provide strong evidence that glucose and streptozotocin act through a common pathway of p135 O-glycosylation that is present only in primary β-cells in islets. The observation that both glucose and streptozotocin stimulate p135 O-glycosylation provides a possible mechanism by which hyperglycemia may cause streptozotocin-like effects in β-cells and thus contribute to the development of type 2 diabetes.

In one embodiment of the present invention, there is provided a method of isolating pancreatic islets so as to protect β-cells from toxicity of nitric oxide and/or streptozotocin-like molecules generated during the isolation process by isolating the islets in the presence of compound (s) that acts through the glucosamine pathway.

In another embodiment of the present invention, islets are isolated in the presence of high glucose (6–300 mM) and glutamine (0.001–300 mM) in order to protect β-cells from toxicity of nitric oxide and/or streptozotocin-like molecules.

In another embodiment of the present invention, islets are isolated in the presence of glucosamine (0.001–300 mM) in order to protect β-cells from toxicity of nitric oxide and/or streptozotocin-like molecules.

In another embodiment of the present invention, islets are isolated in the presence of N-acetylglucosamine (0.001–300 mM) in order to protect β-cells from toxicity of nitric oxide and/or streptozotocin-like molecules.

In another embodiment of the invention, islets are isolated in the presence of nitric oxide (NO) inhibitors such as nitric oxide synthase inhibitors and/or nitric oxide scavengers in order to prevent the formation of nitric oxide and/or streptozotocin-like molecules and protect β-cells.

In another embodiment of the invention, islets are isolated in the presence of high glucose (6–300 mM) and glutamine (0.001–300 mM) and nitric oxide inhibitors in order to protect β-cells from toxicity of nitric oxide and/or streptozotocin-like molecules.

In another embodiment of the invention, islets are isolated in the presence of glucosamine (0.001–300 mM) and nitric oxide inhibitors in order to protect β-cells from toxicity of nitric oxide and/or streptozotocin-like molecules.

In another embodiment of the present invention, islets are isolated in the presence of N-acetylglucosamine (0.001–300 mM) and nitric oxide inhibitors in order to protect β-cells from toxicity of nitric oxide and/or streptozotocin-like molecules.

In another embodiment of the present invention, there is provided a method to determine if nitric oxide and/or streptozotocin-like molecules have damaged islets. Islets are pre-incubated with low glucose (0–6 mM), and then stimulated with low glucose (0–6 mM), high glucose (6–300 mM), glucosamine (0.001–300 mM), N-acetylglucosamine (0.001–300 mM), or streptozotocin (0.001–300 mM). Islet proteins are then analyzed for protein O-glycosylation, wherein no change in O-glycosylation of a 135 kD protein indicates said islets have been damaged with nitric oxide and/or streptozotocin-like molecules.

In another embodiment of the present invention, there is provided a method of assaying isolated islets or beta-cells to determine if candidate diabetes drugs might be effective in treating diabetes. Islets or beta-cells are isolated according to the methods described above, pre-incubated with low glucose (0–6 mM), and then either stimulated with low glucose (0–6 mM), high glucose (6–300 mM), glucosamine (0.001–300 mM), N-acetylglucosamine (0.001–300 mM), or streptozotocin (0.001–300 mM), with or without the drug(s) of interest present. Islet or beta cell proteins are then analyzed for protien O-glycosylation, wherein inhibition of O-glycosylation on a 135 kD protein in the presence of said candidate drug indicates said candidate diabetes drug might be effective in treating diabetes.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows that glucose and glucosamine do not consistently stimulate p135 O-glycosylation in islets isolated in the presence of 5.5 mM glucose and no added L-glutamine. Islets isolated in 5.5 mM glucose and no added L-glutamine (100/condition) were incubated for 60 min with 3 mM glucose (G3), 28 mM glucose (G28), or 15 mM glucosamine (GlcN). At the end of the incubation period, supernatant was removed for insulin measurement, and O-glycosylated proteins were immunoprecipitated with RL2 antibody. Immunoprecipitated proteins were separated and transferred to nitrocellulose for Western blotting with RL2 antibody.

FIG. 2 shows that glucose, glucosamine, and streptozotocin stimulate p135 O-glycosylation in islets isolated in the presence of 11 mM glucose and 1 mM L-glutamine. Islets were isolated as in FIG. 1 except that all isolation buffers were supplemented to contain 11 mM glucose and 1 mM L-glutamine. Following isolation, islets (100/condition) were incubated for 60 min with 3 mM glucose (G3), 28 mM glucose (G28), 15 mM glucosamine (GlcN), or 5 mM streptozotocin (STZ). At the end of the incubation period, the supernatant was removed for insulin measurement, and O-glycosylated proteins were analyzed as in FIG. 1.

FIG. 7 shows that the nitric oxide donors sodium nitroprusside and hydroxylamine do not stimulate p135 O-glycosylation in islets isolated in 11 mM glucose and 1 mM L-glutamine. Islets were isolated as in FIG. 2. Following isolation, islets (100/condition) were incubated for 60 min with 3 mM glucose (G3), the combination of 10 mM sodium nitroprusside and 10 mM hydroxylamine (N/H), or 5 mM streptozotocin (STZ). At the end of the incubation period, supernatant was removed for insulin measurement, and O-glycosylated proteins were analyzed as in FIG. 1.

DETAILED DESCRIPTION OF THE INVENTION

Figure 1A:
FIG. 1A shows results from a representative experiment.

An important link has recently been shown in vivo between β-cell O-linked protein glycosylation and β-cell apoptosis, with hyperglycemia having been demonstrated to reversibly increase β-cell O-linked protein glycosylation by providing substrate for the glucosamine pathway. In contrast, the same study showed that the administration of streptozotocin to rats prior to the induction of hyperglycemia results in irreversible increases in O-glycosylation and subsequent β-cell apoptosis. In light of these data, β-cell O-glycosylation was investigated in vitro by exposing isolated rat islets to high glucose, glucosamine, or streptozotocin and analyzing the pattern of O-glycosylated proteins present. All three compounds acutely increased O-glycosylation of a predominate 135 kD protein (p135). However, their ability to stimulate p135 O-glycosylation was only consistently observed when islets were isolated in the presence of high glucose and 1 mM L-glutamine. Islets isolated in low glucose and no added L-glutamine demonstrated no consistent increase in p135 O-glycosylation in response to glucose, glucosamine, or streptozotocin. These data suggest that during islet isolation, β-cell enzymes responsible for regulating p135 O-glycosylation may be adversely affected by the absence of high glucose and glutamine, which together are necessary for O-linked N-acetylglucosamine synthesis.

It is proposed that this toxicity occurs because, during standard islet isolation, islets are exposed to low glucose (5.5 mM) and no added glutamine. Therefore the glucosamine pathway will be shut down in the islets and there is little or no O-liked protein glycosylation. The β-cell enzyme O-GlcNAcase that cleaves O-linked N-acetylglucosamine (O-GlcNAc) off protein thus has no substrate to keep it occupied and appears to be vulnerable to attack by nitric oxide and/or streptozotocin-like molecules that form during the isolation process.

In order to protect the islets during the isolation process, the O-GlcNAcase enzyme must be protected. This can be accomplished by adding high glucose and glutamine to the isolation buffers and/or by adding glucosamine or N-acetylglucosamine to the isolation buffers. This causes the β-cell to modify protein with O-linked N-acetylglucosamine (O-GlcNAc), which is the substrate for the GlcNAcase enzyme. Thus, with the GlcNAcase enzyme occupied with its natural substrate, it is less vulnerable to inactivation by nitric oxide and/or streptozotocin-like molecules.

Streptozotocin-like compounds may form as a result of nitric oxide being generated during the isolation process itself. It is likely that the nitric oxide is formed when nitric oxide synthase (NOS) enzymes are liberated from the pancreatic tissue being digested. The nitric oxide can then combine with any number of hexoses or related molecules (that are also released during the digestion) to form streptozotocin-like molecules. Thus, the addition of nitric oxide inhibitors (nitric oxide synthase inhibitors and/or nitric oxide scavengers) to the isolation buffers can further protect the islets.

Therefore, the present invention demonstrates that during standard islet isolation, in which the islets are isolated in low glucose (approximately 5.5 mM) and no added glutamine, nitric oxide and/or streptozotocin-like molecules form and inactivate the β-cell enzyme O-GlcNAcase, which removes O-linked N-acetylglucosamine from proteins. This damage can be largely prevented by occupying the O-GlcNAcase enzyme with substrate (O-linked N-acetylglucosamine or N-acetylglucosamine), which is formed when the islets are isolated in the presence of high glucose and glutamine, or glucosamine, or N-acetylglucosamine, or other compounds acting through the glucosamine pathway. Decreasing formation of nitric oxide and/or streptozotocin-like molecules by adding nitric oxide inhibitors can further prevent the damage. These steps protect the β-cell O-GlcNAcase enzyme during the isolation procedure. Failure to take these precautions, as has been done for at least the last 30 years, results in islets that for all intents and purposes respond to glucose and glucosamine as though they have been treated with streptozotocin and which are not optimal or even desirable for the experimental study of diabetes drugs or isolating islets for transplantation.

Results disclosed in the present invention can also be used to assess overall islet viability and to assess candidate diabetes drugs for possible affect on β-cell O-linked protein glycosylation. A protein band of 135 kD is detected by immunoprecipitation and Western blotting with RL2 antibody (which binds to O-linked N-acetylglucosamine) after stimulation with high glucose, glucosamine, or streptozotocin. The increased O-linked protein glycosylation on p135 can only be clearly seen, however, when the islets are adequately protected during the isolation process as described above. Without adequate protection the band appears essentially the same in all lanes, suggesting that the islets have already been exposed to streptozotocin-like molecules. Obviously, in order to screen potential diabetes drugs, one would not want to work with streptozotocin-treated islets.

In one embodiment of the present invention, there is provided a method of isolating pancreatic islets that protects β-cells from toxicity of nitric oxide and/or streptozotocin-like molecules generated during the isolation process by isolating the islets in the presence of compound(s) that acts through the glucosamine pathway.

In another embodiment of the present invention, islets are isolated in the presence of high glucose (6–300 mM) and glutamine (0.001–300 mM) in order to protect β-cells from toxicity of nitric oxide and/or streptozotocin-like molecules.

In another embodiment of the present invention, islets are isolated in the presence of glucosamine (0.001–300 mM) in order to protect β-cells from toxicity of nitric oxide and/or streptozotocin-like molecules.

In another embodiment of the present invention, islets are isolated in the presence of N-acetylglucosamine (0.001–300 mM) in order to protect β-cells from toxicity of nitric oxide and/or streptozotocin-like molecules.

In another embodiment of the invention, islets are isolated in the presence of nitric oxide (NO) inhibitors such as nitric oxide synthase inhibitors and/or nitric oxide scavengers in order to prevent the formation of nitric oxide and/or streptozotocin-like molecules and protect β-cells.

In another embodiment of the invention, islets are isolated in the presence of high glucose (6–300 mM) and glutamine (0.001–300 mM) and nitric oxide inhibitors in order to protect β-cells from toxicity of nitric oxide and/or streptozotocin-like molecules.

In another embodiment of the invention, islets are isolated in the presence of glucosamine (0.001–300 mM) and nitric oxide inhibitors in order to protect β-cells from toxicity of nitric oxide and/or streptozotocin-like molecules.

In another embodiment of the present invention, islets are isolated in the presence of N-acetylglucosamine (0.001–300 mM) and nitric oxide inhibitors in order to protect β-cells from toxicity of nitric oxide and/or streptozotocin-like molecules.

In another embodiment of the present invention, there is provided a method to determine if nitric oxide and/or streptozotocin-like molecules have damaged islets. Islets are pre-incubated with low glucose (0–6 mM), and then stimulated with low glucose (0–6 mM), high glucose (6–300 mM), glucosamine (0.001–300 mM), N-acetylglucosamine (0.001–300 mM), or streptozotocin (0.001–300 mM). Islet proteins are then analyzed for protien O-glycosylation, wherein no change in O-glycosylation on a 135 kD protein indicates said islets have been damaged with nitric oxide and/or streptozotocin-like molecules.

In another embodiment of the present invention, there is provided a method of assaying isolated islets or beta-cells to determine if candidate diabetes drugs might be effective in treating diabetes. Islets or beta-cells are isolated according to the methods described above, pre-incubated with low glucose (0–6 mM), and then either stimulated with low glucose (0–6 mM), high glucose (6–300 mM), glucosamine (0.001–300 mM), N-acetylglucosamine (0.001–300 mM), or streptozotocin (0.001–300 mM), with o r without the drug(s) of interest present. Islet or beta cell proteins are then analyzed for protien O-glycosylation, wherein inhibition of O-glycosylation on a 135 kD protein in the presence of said candidate drug indicates said candidate diabetes drug might be effective in treating diabetes.

The following examples are given for the purpose of illustrating various embodiments of the invention and are not meant to limit the present invention in any fashion.

EXAMPLE 1

Islet Isolation

In a typical experiment, islets were isolated aseptically from 3–4 male Sprague-Dawley rats. During surgery, the common bile duct of each pancreas was cannulated, and the pancreas was inflated with 20 ml of Hank's Balanced Salt Solution (HBSS). The distended pancreas was excised, and lymph nodes, fat, blood vessels, and bile ducts were removed under a stereo dissecting microscope. Tissue was chopped extensively and rinsed 5–6 times with HBSS. The tissue was digested with collagenase P (3 mg/ml tissue) at 37° C. for 3–4 min using a wrist action shaker. Digested tissue was rinsed 3–4 times with HBSS, and islets were purified on a discontinuous Ficoll gradient consisting of 27%, 23%, 20.5%, and 11% Ficoll in (25 mM) HEPES-HBSS buffer. Islets were harvested from the gradient and washed once with HBSS. Islets were washed 6 times in DMEM supplemented with 25 mM HEPES pH 7.40, 25 mM $NaHCO_3$, 0.1% bovine serum albumin, 3 mM glucose, and 1 mM L-glutamine (complete DMEM). This isolation procedure typically provided 300–400 islets per rat, which were then used as described below. In selected experiments, islets were isolated as described above, except that all isolation buffers were supplemented t o contain 11 mM glucose and 1 mM L-glutamine.

EXAMPLE 2

Incubation of Islets for Insulin Secretion and Protein O-Glycosylation

Freshly isolated islets were placed into siliconized 16×100-mm round bottom, screw-cap tubes and pre-incubated for 30 min in 1 ml of complete DMEM. For each experiment, 100 islets were placed into each tube. Pre-incubation and all subsequent incubations were performed at 37° C. under an atmosphere of 95% $O_2$/5% $CO_2$. After 30 min, pre-incubation buffer was aspirated, and islets were incubated with complete DMEM supplemented with the appropriate secretagogue. At the end of the incubation period, the entire supernatant was removed for insulin radioimmunoassay. Islets were processed for subsequent immunoprecipitation as described below. For each experiment, insulin secretion in the control sample was set at 100% and all other results were expressed as percentages of control.

EXAMPLE 3

β-TC3 Cell Line Culture

β-TC3 cells (passage 37) were obtained form the University of Pennsylvania Diabetes Center from Dr. D. Hanahan (University of California, San Francisco). β-TC3 cells were cultured in 10-cm dishes in the presence of RPMI 1640 medium supplemented with 10% fetal bovine serum, penicillin (75 μg/ml), streptomycin (50 μg/ml), and 2 mM L-glutamine. Cells were trypsinized and subcloned weekly. Media were changed twice weekly and on the day prior to an experiment, and insulin responsiveness to glucose and carbachol was routinely monitored. Cells were used between passages 38 and 55.

EXAMPLE 4

Incubation of β-TC3 cells for Insulin Secretion and Protein O-Glycosylation

β-TC3 cells in 10-cm dishes were washed three times in Krebs'-HEPES buffer (25 mM HEPES, pH 7.40, 115 mM NaCl, 24 mM $NaHCO_3$, 5 mM KCl, 2.5 mM $CaCl_2$, 1 mM $MgCl_2$) supplemented with 0.1% bovine serum albumin and 1 mM L-glutamine. Cells were pre-incubated in 5 ml of the same buffer for 30 min at 37° C. under an atmosphere of 95% air/5% $CO_2$. After 30 min, the pre-incubation buffer was aspirated and cells were incubated at 37° C. under an atmosphere of 95% air/5% $CO_2$ with 5 ml of Krebs'-HEPES buffer supplemented with the appropriate secretagogue. At the end of the incubation period, supernatant was removed for insulin radioimmunoassay. Cells left in the dishes were processed for subsequent immunoprecipitation as described below.

EXAMPLE 5
Processing of Islets and β-TC3 Cells for Immunoprecipitation of O-Glycosylated Proteins At the end of the experiment, all supernatant was removed from the tubes or dishes. One ml of ice-cold lysis buffer (50 mM HEPES, pH 7.40, 150 mM NaCl, 1% Triton X-100, 5 mM EDTA, 5 mM EGTA, 20 mM NaF, 20 mM $Na_4P_2O_7$, 1 mM $NaVO_4$, 1 mg/ml bacitracin, 1 mM phenylmethylsulfonylfluoride, 1 μg/ml leupeptin, 1 μg/ml aprotinin) was added to each tube or dish. Cells were scraped on ice into 1.5 ml conical screw cap Eppendorf tubes. Borosilicate tubes containing islets were vortexed for 30 sec and placed on ice for 30 min. Islet samples were vortexed for an additional minute before transfer to 1.5-ml conical screw cap Eppendorf tubes. All subsequent immunoprecipitation steps were performed at 4° C. Samples were centrifuged at 10,000×g for 15 min. The supernatant was transferred to a second 1.5-ml conical Eppendorf tube, and O-glycosylated proteins were immunoprecipitated for 2 h on a rocker with 2 μl of mouse monoclonal RL2 antibody, which selectively binds to O-glycosylated protein (21,22). After 2 h, 20 μl of protein A trisacryl beads (Pierce) preadsorbed with 20 μg of rabbit anti-mouse antibody (Sigma) were added to the tubes and the incubation was continued for an additional 2 hours. At the end of the incubation, beads were washed once with Wash Buffer 1 (150 mM NaCl, 10 mM HEPES, pH 7.40, 1% Triton X-100, and 0.1% SDS) and once with Wash Buffer 2 (10 mM HEPES, pH 7.40, 1% Triton X-100, and 0.1% SDS). After the final washing step, 25 μl of 2× sample buffer (100 mM Tris, pH 6.80, 4% SDS, 20% glycerol, and 20 μg/liter bromophenol blue) was added to each tube. Samples were vortexed for 30 sec, boiled for 5 min, and stored at −20° C. prior to subsequent analysis.

EXAMPLE 6
Western Blotting of Samples

Samples were loaded onto 7.5% SDS-polyacrylamide gels. Colored molecular weight markers (Amersham) were run on each gel. Proteins were separated for 1 h at 175 V at room temperature using a Bio-Rad Mini-PROTEAN II dual slab cell. Proteins were transferred to ECL nitrocellulose paper (Amersham) for 1.5 h (100 V, 4° C.). Nitrocellulose blots were blocked for 1 h at room temperature in blocking buffer (5% bovine serum albumin in 10 mM Tris, pH 7.40, 150 mM NaCl, 0.1% sodium azide, 0.05% Tween 20). After blocking, the blots were probed with RL2 antibody (1:1000 dilution in blocking buffer) for 1 h at room temperature. Blots were washed 6 times (5 min each) with TBST (10 mM Tris pH 7.40, 150 mM NaCl, 0.05% Tween 20). After washing, blots were probed with horseradish peroxidase conjugated sheep anti-mouse antibody (Amersham) at a 1:1500 dilution in TBST for 1 h at room temperature. Blots were washed again as above and developed with ECL reagent (Amersham). After air-drying, blots were exposed to Bio-Max X-ray film (Kodak). For each experiment, the intensity of the control sample was set at 100% and all other results were expressed as percentages of control.

EXAMPLE 7
O-Linked N-acetylglucosamine Transferase (OGT) Assay

O-Linked N-acetylglucosamine transferase activity was measured in islets isolated in the presence of either 5.5 mM glucose and no added L-glutamine or 11 mM glucose and 1 mM L-glutamine. Following isolation, islets were incubated for 30 minutes, in low glucose and 1 mM L-glutamine to allow baseline O-glycosylation of islet proteins to occur and maximize detection of O-glycosylation of added exogenous substrate. Islets were homogenized in 50 mM Tris-HCl, pH 7.40 containing 12.5 mM $MgCl_2$. Homogenates were spun at 100,000×g for 30 minutes at 4° C. to remove membranes containing N-glycosylated proteins. Supernatants containing OGT were incubated with 5 μg recombinant SpE, (a Sp1-derived substrate for OGT) and 2.5 μCi UDP-[$^3$H]GlcNAc (Sigma) for 30 minutes at 37° C. After stopping the reaction, [$^3$H]GlcNAc incorporated into protein was quantitated by TCA precipitation followed by liquid scintillation spectrometry.

EXAMPLE 8
Data Analysis

Films were photographed using a Sony digital camera, and intensities of bands present on films were quantitated using the program NIH Image. All results are expressed as the mean±SEM, using the Windows-compatible version 2.98 of the program FigP (Biosoft, St. Louis, Mo.). Statistical analysis was performed using the same program. Data were analyzed by one-way analysis of variance followed by multiple comparisons between the means using the least significant difference test. A probability of p<0.05 was considered to indicate statistical significance.

EXAMPLE 9
Increased protein O-glycosylation in β-cells

In cell types such as BSC40 cells or vascular smooth muscle cells, treatment with glucose or glucosamine has been shown to cause the accumulation of O-glycosylated protein in vitro after the cells have been artificially starved of GlcNAc for several hours (21). In order to determine if similar increased protein O-glycosylation occurred in β-cells, pancreatic islets were isolated in Hank's Balanced Salt Solution (HBSS) containing low (5.5 mM) glucose and no added L-glutamine, to prevent GlcNAc synthesis. After isolation, islets were stimulated (in the presence of 1 mM L-glutamine) for one hour with 3 mM glucose, 28 mM glucose, or 15 mM glucosamine. After incubation, immunoprecipitation was performed with RL2 antibody, which selectively binds O-glycosylated protein (21,22,24). Following immunoprecipitation, Western blotting was performed with the same antibody.

Figure 1B:
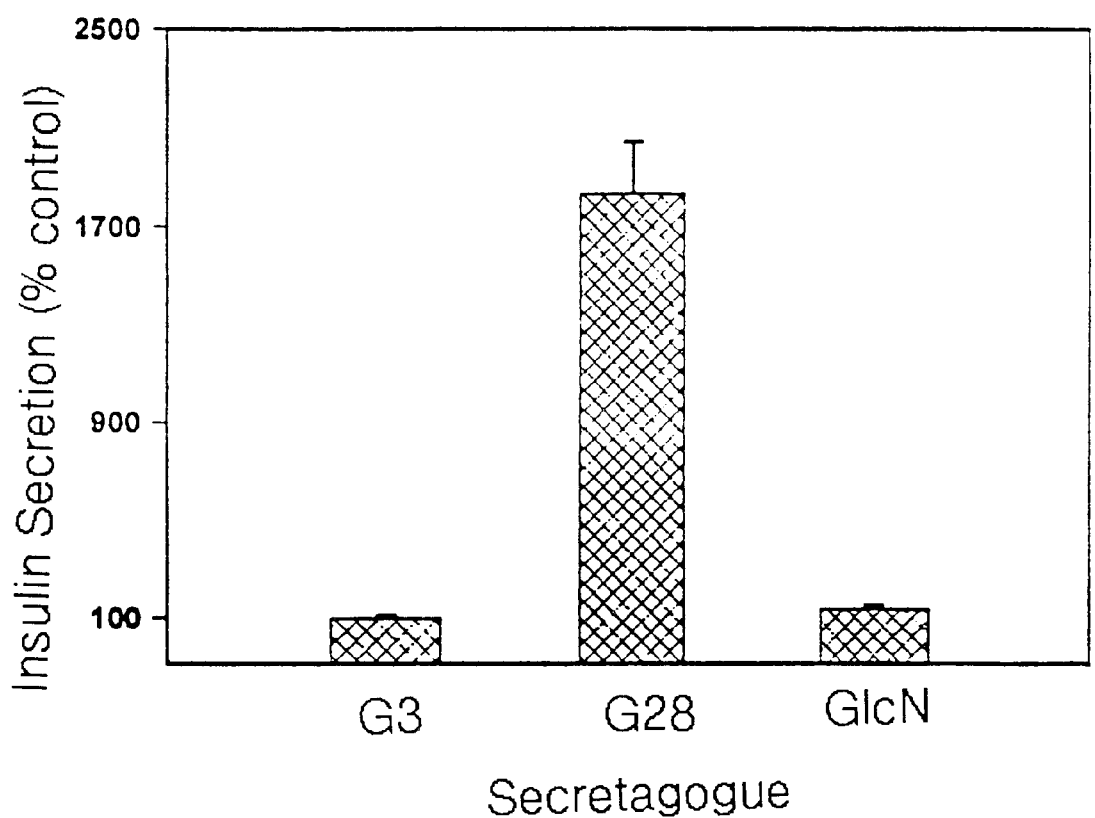
FIG. 1B shows insulin secretion data corresponding to 1A.

FIG. 1 shows results from a representative experiment. Immunoprecipitation and subsequent Western blotting with RL2 antibody demonstrated that islets contained a predominate 135 kD O-glycosylated protein (p135). In the case of non-immune immunoprecipitation or immunoprecipitation with an irrelevant mouse monoclonal antibody of the same subclass as RL2, p135 was not detected. No consistent increased p135 O-glycosylation was observed after stimulation of islets with either 28 mM glucose or 15 mM glucosamine. Based on their ability to secrete insulin (FIG. 1), the isolated islets appeared to be glucose-responsive. Islets stimulated with 28 mM glucose demonstrated an 1831.6±212.2% increase in insulin secretion compared to the 3 mM glucose control (p<0.05).

Figure 2A:
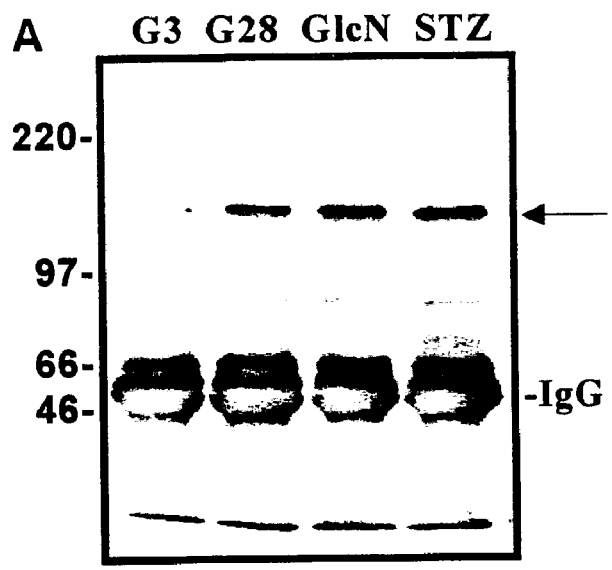
FIG. 2A shows results from a representative experiment.
Figure 2B:
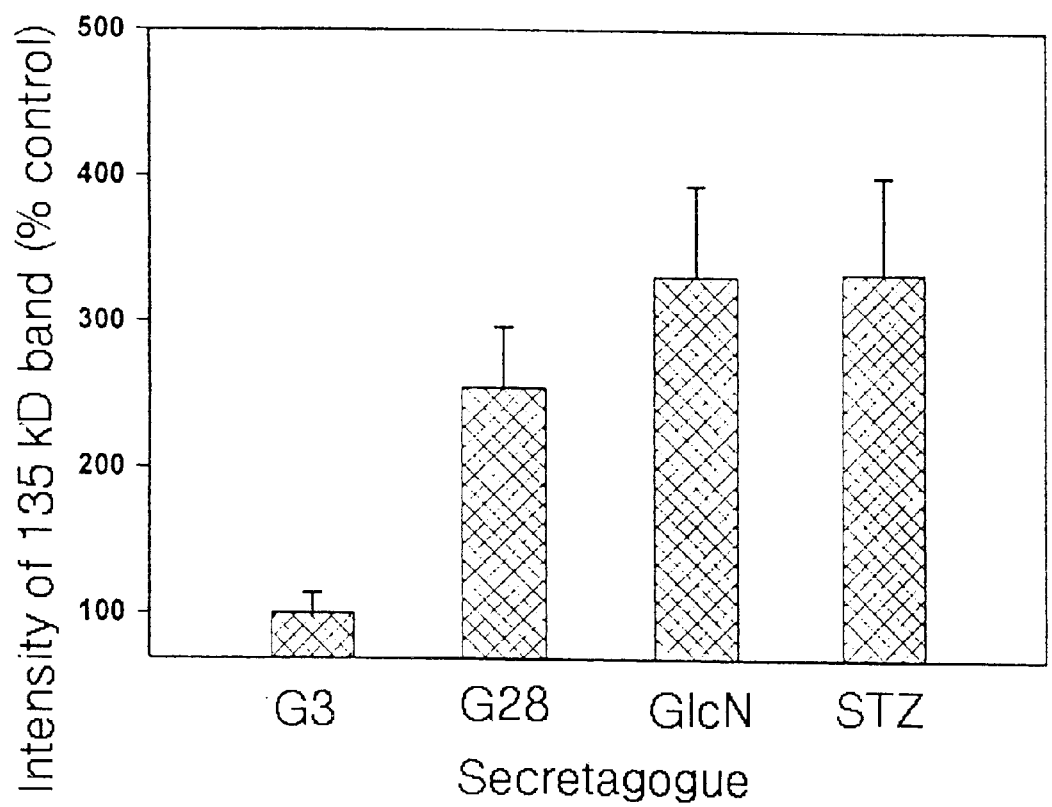
FIG. 2B shows results from 2A in which the intensity of the band is shown as the mean±SE from 10 sets of observations from 3 independent experiments.
Figure 2C:
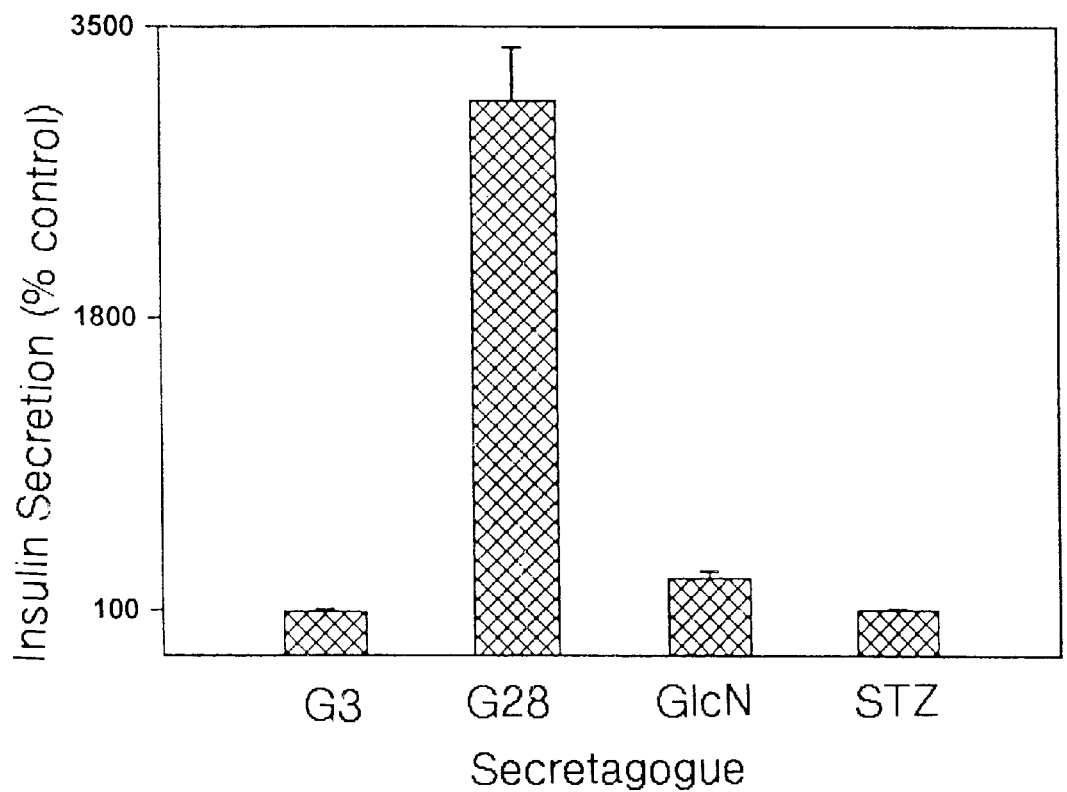
FIG. 2C shows insulin secretion data corresponding to 2B.

In contrast, when islets were isolated in HBSS supplemented to contain 11 mM glucose and 1 mM L-glutamine (to promote GlcNAc synthesis), different results were obtained. As FIG. 2 shows, after isolation in 11 mM glucose and 1 mM L-glutamine, islets responded to 28 mM glucose by increasing p135 O-glycosylation 255.2±41.1% compared to 3 mM glucose (p<0.05). In addition, islets responded to 15 mM glucosamine with a 331.9±61.9% increase in p135 O-glycosylation (p<0.05 versus control). Also shown in FIG. 2, streptozotocin stimulated an increase in p135 O-glycosylation by 333.9±66.8% (p<0.05 versus control), comparable to that seen with glucosamine. Insulin secretion, in contrast, was again markedly stimulated only by 28 mM glucose (3064±311.8%, p<0.05 versus control).

Figure 3:
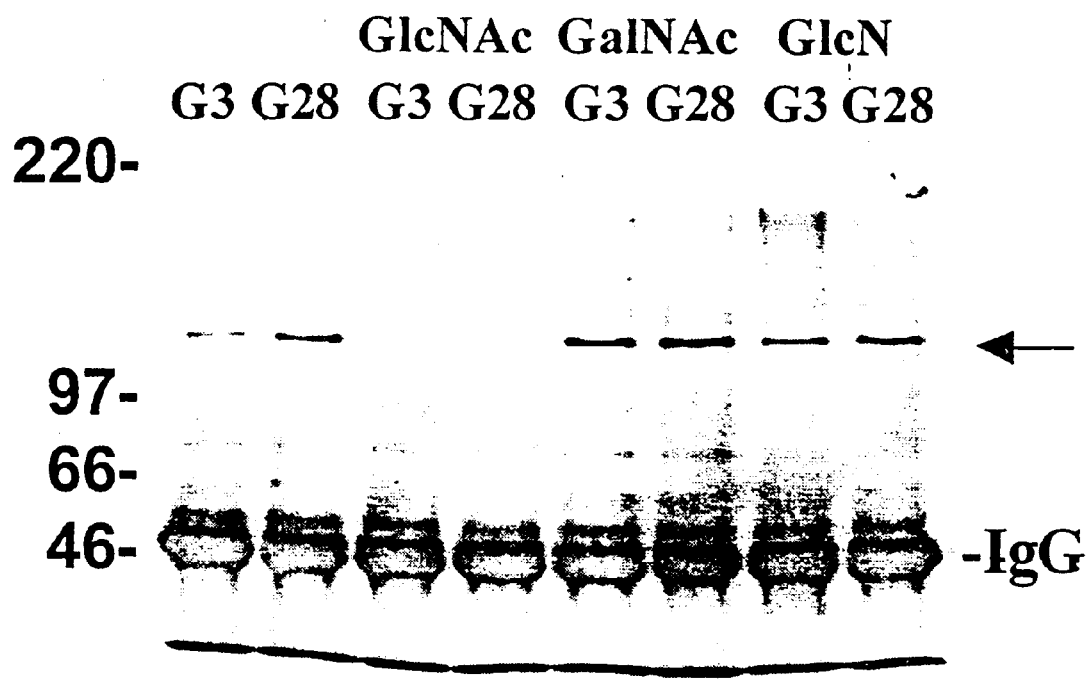
FIG. 3 shows that N-acetylglucosamine (GlcNAc) selectively blocks binding of RL2 antibody to p135. Islets (100/condition) were incubated for 60 min with either 3 mM glucose (G3) or 28 mM glucose following pre-incubation with 5 mM streptozotocin (STZ). At the end of the incubation period, O-glycosylated proteins were immunoprecipitated with RL2 antibody in the presence of 0.3 M N-acetylglucosamine (GlcNAc), 0.3 M N-acetylgalactosamine (GalNAc), or 0.3 M glucosamine (GlcN) and analyzed by Western blotting as described in FIG. 1.

In order to confirm that RL2 binding was selective for O-GlcNAc modified protein, N-acetylglucosamine (GlcNAc), N-acetylgalactosamine (GalNAc), and glucosamine itself were added during the RL2 immunoprecipitation step. As can be seen in FIG. 3, addition of GlcNAc completely inhibited immunoprecipitation of p135. In contrast, neither GalNAc nor glucosamine added at the same concentration as GlcNAc prevented RL2 antibody from immunoprecipitating the protein. Together with the data shown in FIG. 2, these results demonstrated that glucose, glucosamine, and streptozotocin selectively increased the O-linked N-acetylglucosamine content of p135 in islets.

In order to investigate the possibility that increased p 135 O-glycosylation was the result of enhanced O-GlcNAc transferase activity due to the modified method of islet isolation, O-linked N-acetylglucosamine transferase activity was measured in islets isolated in the presence or absence of 11 mM glucose and 1 mM L-glutamine. As Table 1 shows, [$^3$H]GlcNAc incorporation into exogenous protein substrate by OGT-containing cytosol obtained from 500 islets isolated by either method was only marginally above background, suggesting that prohibitive numbers of islets may be required for direct measurement of islet O-linked N-acetylglucosamine transferase activity.

The most likely explanation for the data shown in FIGS. 2 and 3 was that glucose and glucosamine were providing more substrate for β-cell O-GlcNAc transferase (OGT) while streptozotocin was inhibiting βO-GlcNAcase. In each case, the end result would be an increase in p135 O-glycosylation. In order to test this idea, islets were incubated with glucose, glucosamine, and streptozotocin in the presence and absence of 6-diazo-5-oxonorleucine (DON), a glutamine analog inhibitor o f glutamine:fructose-6-phosphate amidotransferase (GFAT).

Figure 4:
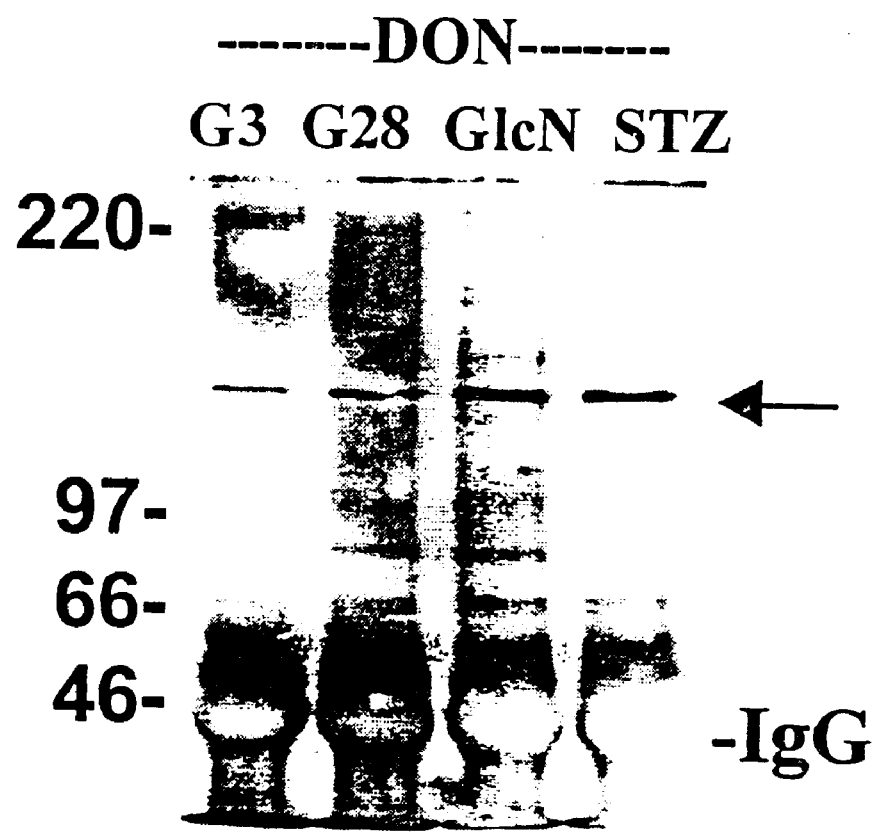
FIG. 4 shows that the glutamine:fructose-6-phosphate inhibitor 6-diazo-5-oxonorleucine (DON) inhibits glucose but not glucosamine or streptozotocin-induced p135 O-glycosylation. Islets (100/condition) were incubated for 60 min with either 3 mM glucose (G3), 28 mM glucose (G28), 15 mM glucosamine (GLCN), or 5 mM streptozotocin (STZ) in the presence or absence of 100 µM of the glutamine:fructose-6-phosphate inhibitor 6-diazo-5-oxonorleucine (DON). At the end of the incubation period, O-glycosylated proteins were immunoprecipitated and analyzed by Western blotting as described in FIG. 1. Results shown are representative of duplicate sets of observations.

As shown in FIG. 4, addition of 6-diazo-5-oxonorleucine inhibited the glucose-induced O-glycosylation of p135, suggesting that glucose acts through the glucosamine pathway to provide more substrate for OGT. In contrast, glucosamine was still able to stimulate p135 O-glycosylation in the presence of 6-diazo-5-oxonorleucine, most likely because the addition of glucosamine bypasses GFAT. Likewise, streptozotocin was also able to increase p135 O-glycosylation in the presence of 6-diazo-5-oxonorleucine, in agreement with a previous report that streptozotocin increases protein O-glycosylation by inhibiting removal of O-linked GlcNAc from protein (21).

EXAMPLE 10

Streptozotocin-induced p135O-glycosylaton

In order to investigate further streptozotocin-induced p135 O-glycosylation, islets were pre-incubated in the presence or absence of streptozotocin and then stimulated with either 3 or 28 mM glucose. Following this stimulation, islets were then incubated for an additional 30 min in 3 mM glucose.

Figure 5:
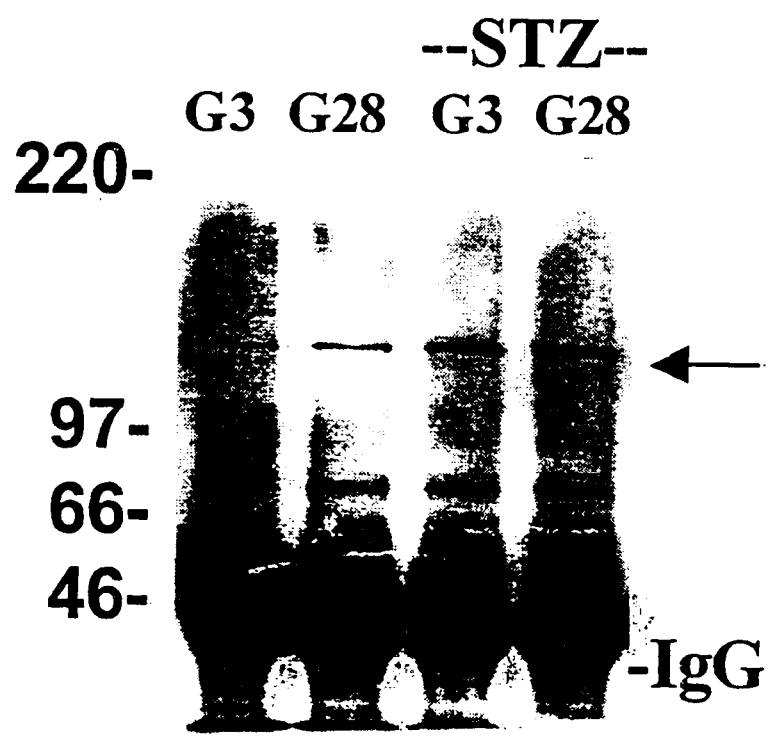
FIG. 5 shows that glucose-induced p135 O-glycosylation is reversible while streptozotocin-induced p135 O-glycosylation is irreversible. Islets (100/condition) were pre-incubated for 30 min with either 3 mM glucose or 5 mM streptozotocin (STZ). Islets were then incubated for 30 min with either 3 mM glucose (G3) or 28 mM glucose (G28). Afterward, all islets were incubated in 3 mM glucose for an additional 30 min. O-glycosylated proteins were immunoprecipitated and analyzed by Western blotting as described in FIG. 1. Results shown are representative of 4 sets of observations.

As FIG. 5 demonstrates, O-glycosylation of p135 is reversible when islets are stimulated with 28 mM glucose in the absence of streptozotocin and then exposed to low glucose for an additional 30 min. In contrast after exposure to streptozotocin, increased O-glycosylation of p135 is not readily reversible after stimulation with either 3 or 28 mM glucose, suggesting that streptozotocin may act by irreversibly inhibiting β-cell O-GlcNAcase.

Figure 6:
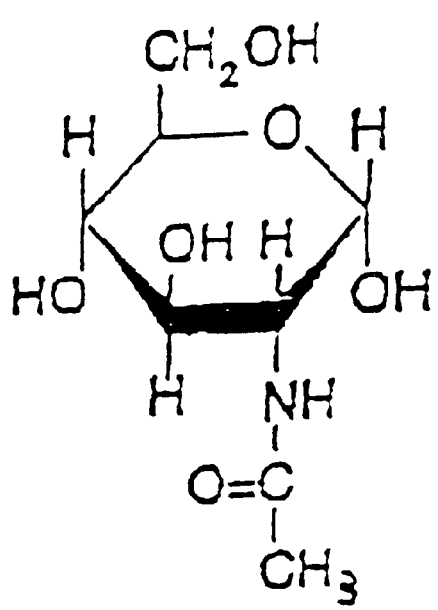
FIG. 6 shows the chemical structures of N-acetylglucosamine (GlcNAc) and streptozotocin (STZ). In streptozotocin, a nitrosourea group corresponds to the acetate present in N-acetylglucosamine.
Figure 6:
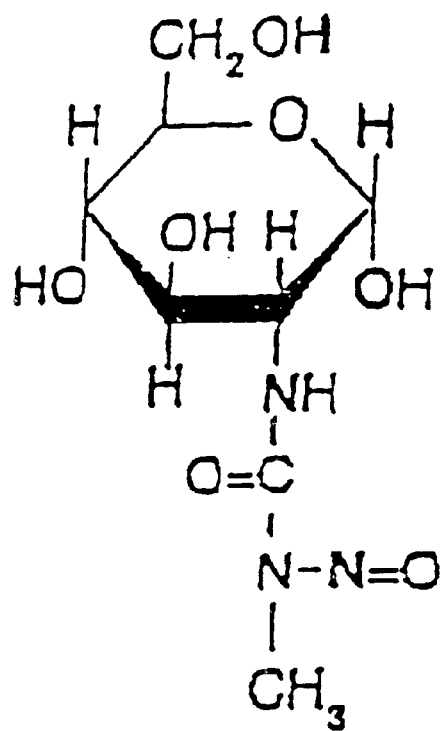

The chemical structure of streptozotocin is shown in FIG. 6 and is remarkably similar to that of N-acetylglucosamine (GlcNAc). In streptozotocin, however, a nitrosourea group corresponds to the acetate present in N-acetylglucosamine (23). It was observed that during the experiments shown in FIG. 2, after an hour of incubation with streptozotocin, the capped islet tubes contained a complete rim of bubbles at the supernatant/air interface. This was only observed with 5 mM streptozotocin and was not seen with glucose or glucosamine. This observation, together with the ability of streptozotocin to serve as a nitric oxide donor, suggested that streptozotocin may have inhibited islet O-GlcNAcase enzyme by releasing nitric oxide.

Figure 7A:
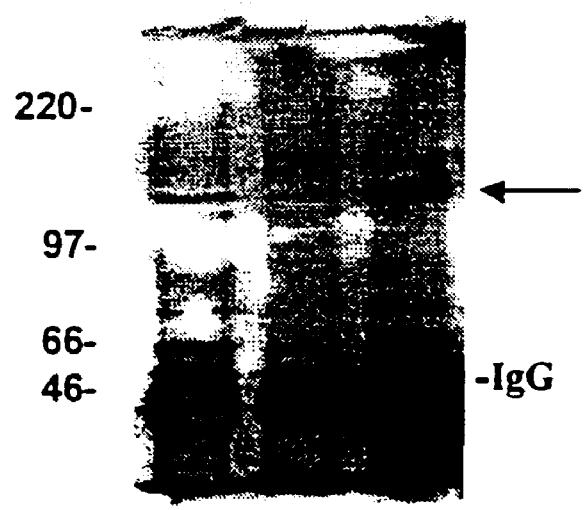
FIG. 7A shows results from a representative experiment.
Figure 7B:
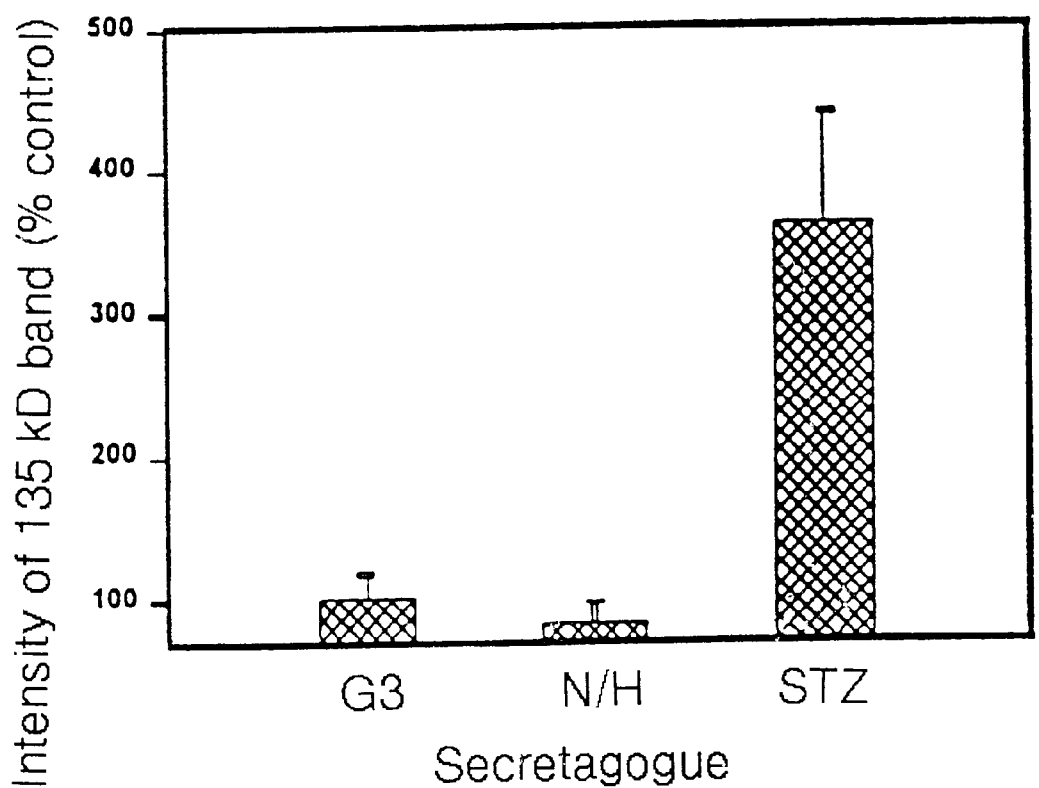
FIG. 7B shows results from FIG. 7A in which the intensity of the band is shown as the mean±SE from 6 sets of observations from 2 independent experiments.

To examine this idea, islets isolated in 11 mM glucose and 1 mM L-glutamine were exposed to either 3 mM glucose, 5 mM streptozotocin, or the (nitric oxide donor) combination of 10 mM sodium nitroprusside and 10 mM hydroxylamine. As shown in FIG. 7, while streptozotocin increased p135 O-glycosylation by 361.3±78.8% compared to control (p<0.05), the combination of sodium nitroprusside and hydroxylamine was without effect. This was despite the fact that after a one-hour incubation, tubes containing sodium nitroprusside and hydroxylamine demonstrated more bubbles at the supernatant/air interface than tubes containing streptozotocin. These data suggested that streptozotocin does not increase p135 O-glycosylation simply by releasing nitric oxide non-specifically in islets, but that streptozotocin's chemical similarity to N-acetylglucosamine may be necessary for its effect.

Data shown in FIG. 2 suggested that increased p135 O-glycosylation may not stimulate insulin secretion from islets. To further investigate the relationship between p135 O-glycosylation and insulin secretion, the effect of 5-diazo-oxo-norleucine (DON), a glutamine analog inhibitor of the enzyme glutamine:fructose-6-phosphate amidotransferase (GFAT), on insulin secretion was examined.

As shown in Table 2, addition of 5-diazo-oxo-norleucine under conditions that completely blocked 28 mM glucose-induced p135 O-glycosylation but not glucosamine or streptozotocin-induced p135 O-glycosylation (24) had no significant effect on glucose-induced insulin secretion. In the absence of 5-diazo-oxo-norleucine, 28 mM glucose induced an 1886.4±79.7% increase in insulin secretion compared to control. In the presence of 5-diazo-oxo-norleucine a similar increase of 2008.9±80.8% was observed after stimulation with 28 mM glucose, supporting the idea that increased p135 O-glycosylation does not acutely stimulate insulin secretion.

The above data suggested that increased p135 O-glycosylation in response to glucose (and glucosamine and streptozotocin) may be an important intracellular pathway in β-cells. To investigate whether this pathway might also be active in clonal β-cell lines, O-glycosylation in response to glucose, glucosamine, and streptozotocin was examined in the β-TC3 insulinoma cell line. β-TC3 cells have previously been shown to secrete insulin in response to stimulation with glucose and carbachol. Importantly, β-TC3 cells also undergo increased tyrosine phosphorylation of a 125 kD protein in response to glucose, similar to that observed in isolated islets.

Figure 8:
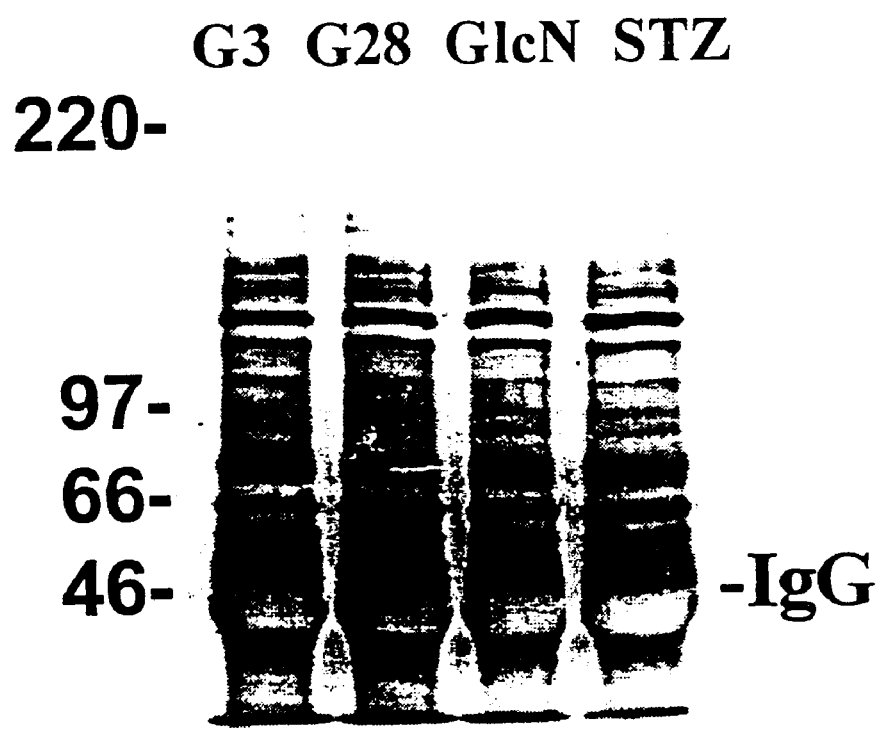
FIG. 8 shows that glucose, glucosamine, and streptozotocin fail to stimulate p135 O-glycosylation in β-TC3 cells. β-TC3 cells grown in culture in 10-cm dishes were pre-incubated for 30 min in 0 mM glucose. Following pre-incubation, the cells (1 dish/condition) were incubated for 60 min with 0 mM glucose (G0), 28 mM glucose and 0.5 mM carbachol (G28), 15 mM glucosamine (GLCN), or 5 mM streptozotocin (STZ). At the end of the incubation period, O-glycosylated proteins were immunoprecipitated and analyzed by Western blotting as described in FIG. 1.

As FIG. 8 shows, however, β-TC3 cells fail to undergo increased O-glycosylation in response to glucose, glucosamine, or streptozotocin. In addition, the pattern of protein O-glycosylation observed in β-TC3 cells was much different than that seen in islets. Whereas islets contained a single responsive O-glycosylated protein (p135), β-TC3 cells contained numerous O-glycosylated proteins that failed to undergo any change in their level of O-glycosylation in response to glucose, glucosamine, or streptozotocin. Similar results were also obtained with an additional β-cell line (HIT cells, data not shown). Together, these findings suggested that regulated p135 O-glycosylation may be an important characteristic that separates actual primary β-cells from β-cell lines grown in culture.

TABLE 1

O-Linked N-acetylglucosamine Transferase Activity In Isolated Islets

| Tissue Source | [$^3$H]GlcNAc Incorporation (cpm) |
|---|---|
| Islets isolated in 5.5 mM glucose and no added L-glutamine | 116.6 ± 0.8 |
| Islets isolated in 11 mM glucose and 1 mM L-glutamine | 142.6 ± 10.6 |
| β-TC3 insulinoma cells | 213.9 ± 6.7 |
| None | 100.1 ± 1.1 |

O-linked N-acetylglucosamine transferase (OGT) activity was measured in islets isolated in the presence of either 5.5 mM glucose and no added L-glutamine or 11 mM glucose and 1 mM L-glutamine. Following isolation, OGT-containing cytosol obtained from 500 isolated islets was incubated with 5 μg recombinant SpE, and 2.5 μCi UDP-[$^3$H]GlcNAc for 30 minutes at 370° C. After stopping the reaction, [$^3$H]GlcNAc incorporation was quantitated. For comparison, OGT-containing cytosol from one 10-cm dish of confluent β-TC3 insulinoma cells was also assayed in the same manner. Results are shown as the mean±SEM from duplicate sets of observations.

TABLE 2

Insulin Secretion In Isolated Islets

| Condition | DON | Insulin |
|---|---|---|
| 3 mM glucose | 0 | 100.0 ± 39.4 |
| 3 mM glucose | 100 | 160.6 ± 50.5 |
| 28 mM glucose | 0 | 1886.4 ± 79.7 |
| 28 mM glucose | 100 | 2008.9 ± 80.8 |
| 15 mM glucosamine | 0 | 244.9 ± 101.1 |
| 15 mM glucosamine | 100 | 314.5 ± 166.2 |
| 5 mM streptozotocin | 0 | 147.1 ± 16.8 |
| 5 mM streptozotocin | 100 | 115.6 ± 7.8 |

Inhibition of the enzyme glutamine:fructose-6-phosphate transferase (GFAT) does not affect insulin secretion from isolated in 11 mM glucose and 1 mM L-glutamine. Following isolation as in FIG. 2, islets (100/condition) were incubated for 60 min with 3 mM glucose, 28 mM glucose, 15 mM glucosamine, o r 5 mM streptozotocin ±100 μM 5-diazo-oxonorleucine (DON), a glutamine analog inhibitor of GFAT. At the end of the incubation period, supernatant was removed for insulin measurement. Results are shown as the mean±SEM from duplicate sets of observations.

Discussion

The results shown above demonstrate that glucose, glucosamine, and streptozotocin stimulate p135 O-glycosylation in isolated islets in the presence of 11 mM glucose and 1 mM L-glutamine. Islets isolated in 5.5 mM glucose and no added L-glutamine showed no consistent increase in p135 O-glycosylation in response to glucose or glucosamine.

The results shown above also demonstrate that glucose, glucosamine and streptozotocin act through a common pathway in β-cells of pancreatic islets by selectively increasing O-glycosylation of a 135 kD protein. Importantly, the phenomenon of acutely increased p135 O-glycosylation in response to glucose, glucosamine and streptozotocin appears to be specific for islets. Regulated p135 O-glycosylation was not found to occur in clonal insulinoma cell lines, indicating that the pathway may be a characteristic that distinguishes actual β-cells from clonal β-cell lines.

It is hypothesized that the ability of isolated pancreatic islets to regulate protein O-glycosylation in the same manner as observed in vivo (23) is compromised by the combination of low glucose and no L-glutamine being present during the process of islet isolation. Under these conditions, because L-glutamine is required for synthesis of N-acetylglucosamine (GlcNAc) from glucose, islets go several hours without being able to synthesize GlcNAc. In this case, the enzyme involved in attaching O-GlcNAc to protein, O-linked N-acetylglucosamine transferase (OGT) might be relatively deprived of its natural substrate. In the harsh process of collagenase digestion during islet isolation and in the absence of normal substrate, the activity of this enzyme might therefore be compromised.

This possibility, however, could not be confirmed by direct measurement of O-linked N-acetylglucosamine transferase activity performed following islet isolation, due to the fact that even though islets are enriched in O-linked N-acetylglucosamine transferase (21), relatively small numbers of islets are obtained when performing rodent islet isolation. Thus, methodology of direct measurement of O-linked N-acetylglucosamine transferase activity, which is suitable for assaying purified or recombinant O-linked N-acetylglucosamine transferase (25,26), appears to be limited in the case of islets by the amount of tissue that can be obtained. In addition, measurement of islet O-linked N-acetylglucosamine transferase activity is also complicated by the fact that endogenous non-radiolabeled UDP-GlcNAc is present in the OGT-rich cytosolic fraction prepared from islets. It is also possible that the addition of 11 mM glucose and 1 mM L-glutamine during islet isolation preserves the ability of islets to regulate O-glycosylation not by protecting O-linked N-acetylglucosamine transferase but instead by protecting other enzymes involved in O-GlcNAc turnover such as O-GlcNAc-selective N-acetylβ-D-glucosaminidase (O-GlcNAcase).

Based on the results obtained when islets were incubated in the presence and absence of the glutamine:fructose-6-phosphate amidotransferase (GFAT) inhibitor 6-diazo-5-oxonorleucine (DON), glucose and glucosamine appear to increase p135 O-glycosylation by providing more UDP-N-acetylglucosamine (UDP-GlcNAc) substrate for the enzyme O-GlcNAc transferase to attach to p135. This substrate-driven change, at least in the case of glucose, appears to be reversible. In the case of streptozotocin, however, the O-GlcNAcase enzyme that cleaves O-linked N-acetylglucosamine O-GlcNAc) off p135 appears to be irreversibly inhibited and O-glycosylated protein accumulates.

A dose of 50–100 mg/kg of streptozotocin, administered to a rat is known to cause death of most of the β-cells within 8 hours and the development of diabetes. Streptozotocin has been shown to act by inhibiting the enzyme O-GlcNAc-selective N-acetyl-β-D-glucosaminidase (0-GlcNAcase), which cleaves O-linked N-acetylglucosamine off protein (21,22). By inhibiting this enzyme, streptozotocin increases β-cell O-linked protein glycosylation in vivo as detected by RL2 staining of histologic sections of pancreas (21,23). Furthermore, this increased protein O-glycosylation has been related to β-cell apoptosis in vivo (23). In light of these recent reports, it seems possible that streptozotocin may also cause p135 O-glycosylation in vitro by inhibiting the β-cell enzyme O-GlcNAc-selective N-acetyl-β-D-glucosaminidase (O-GlcNAcase), which removes O-GlcNAc from protein (21). By doing so in isolated islets, streptozotocin apparently causes an accumulation of O-glycosylated p135, even in the presence of baseline 3 mM glucose.

As shown in FIG. 6, streptozotocin has a chemical structure that resembles N-acetylglucosamine (GlcNAc) and contains a nitrosourea group that can release a molecule of nitric oxide (27). This has led several investigators to suggest that streptozotocin may exert its effects on β-cells by acting as a nitric oxide donor (27–29). In light of the fact the O-GlcNAcase enzyme contains a free sulfhydryl group in its active site (30), it seems possible that streptozotocin might be acting as a suicide substrate by S-nitrosylating the enzyme (31–34). The above observation that the nonspecific nitric oxide donors sodium nitroprusside and hydroxylamine did not increase p135 O-glycosylation supports the idea that unique structural properties of streptozotocin must be required for its effects.

Insulin secretion data suggest that increased p135 O-glycosylation does not appear to stimulate insulin secretion in the short term, but does not rule out a possible role in long-term glucose sensing. Regardless of the necessity of p135 O-glycosylation for insulin secretion, this pathway may still be critical in β-cells in light of in vivo observations (23) and the fact that glucosamine has been proposed to mediate maladaptive changes in β-cells in response to prolonged hyperglycemia (35–37). In other cell types, such as insulin sensitive cells, exposure to both glucose and glucosamine has been shown to increase insulin resistance (38–43). The observation that inhibition of GFAT blocks the effect of glucose on insulin sensitivity suggests that glucose may increase insulin resistance through the glucosamine pathway (44,45). These studies indicate that glucosamine may play a role in energy homeostasis, but the exact mechanism by which glucosamine exerts its effects is not completely understood, as evidenced by a recent report showing that glucosamine may act in 3T3-L1 adipocytes by decreasing ATP levels (46).

The observation that glucose, glucosamine, and streptozotocin can each stimulate O-glycosylation of the same target protein in islets in vitro provides a possible mechanism by which hyperglycemia may cause streptozotocin-like effects in β-cells and thus contribute to the development of type 2 diabetes. In light of this, p135 O-glycosylation in islets may be important since β-cells have been shown to contain much more O-GlcNAc transferase (OGT) than any other cell type. Thus, p135 O-glycosylation may play a role in the progression of type 2 diabetes in humans as well as in the development of streptozotocin-induced diabetes in animals.

Importantly, this mechanism is most consistently observed when islets are isolated in the presence of high glucose and L-glutamine, suggesting that GlcNAc synthesis during islet isolation itself may affect this pathway. The fact that islets isolated in high glucose and 1 mM L-glutamine mimic the O-glycosylation response of islets in vivo to glucose and streptozotocin suggests that these isolation conditions may be more optimal for in vitro studies of pancreatic β-cell protein O-glycosylation.

The following references were cited herein:

1 Dagogo-Jack and Santiago. *Arch Int Med* 1997; 157:1802–1817.
2 Polonsky et al. *New Eng J Med* 1996; 334:777–783.
3 Poitout et al. *J Clin Invest* 1996; 97:1041–1046.
4 Leahy et al. Diabetes Care 1992; 15:442–455.
5 Moran et al. *J Clin Invest* 1997; 99:534–539.
6 Giaccari et al. *Diabetologia* 1995; 38:518–524.
7 Balkan and Dunning. *Diabetes* 1994; 43:1173–1179.
8 McKnight et al. *J Biol Chem* 1992; 267:25208–25212.
9 Sayeski et al. *Nuc Acid Res* 1997; 25:1458–1466.
10 Sayeski et al. *Gene* 1994; 140:289–290.
11 Hart, G. W. *Ann Rev Biochem* 1997; 66:315–335.
12 Starr and Hanover. *J Biol Chem* 1990; 265:6868–6873.
13 Snow et al. *J Cell Biol* 1987; 104:1143–1156.
14 Jackson and Tjian. *Cell* 1988; 55:125–133.
15 Reason, et al. *J Biol Chem* 1992; 267:16911–16921.
16 Chou et al. *J Biol Chem* 1995; 270:18961–18965.
17 Jiang and Hart. *J Biol Chem* 1997; 272:2421–2428.
18 Han and Kudlow. *Mol Cell Biol* 1997; 17:2550–2558.
19 Roos et al. *Mol Cell Biol* 1997; 17:6472–6480.
20 Kreppel et al. *J Biol Chem* 1997; 272:9308–9315.
21 Roos et al. *Proc Assoc Amer Phys* 1998; 110:1–11.
22 Hanover et al. *Arch Biochem Biophys* 1999; 367:51–60.
23 Liu et al. *Proc. Nat. Acad. Sci.* 2000; 97:2820–2825.
24 Konrad et al. *Biochem Biophys Res. Comm.* 2000; 267:26–32.
25 Lubas et al. *Biochemistry* 1995; 34:1686–1694.
26 Haltiwanger et al. *J Biol Chem* 1992; 267:9005–9013.
27 Herr et al. *J Amer Chem Soc* 1967; 89:4808–4809.
28 Turk et al. *Biochem Biophys Res Comm* 1993; 197:1458–1464.
29 Kaneto et al. *Diabetes* 1995; 44:733–738.
30 Dong and Hart. *J Biol Chem* 1994; 269:19321–19330.
31 Melino et al. *Nature* 1997; 388:432–433.
32 Su et al. *Nature* 1994; 370:575–578, 1994.
33 Caselli et al. *J Biol Chem* 1998; 273:32554–32560.
34 Caselli et al. *J Biol Chem* 1994; 269: 24878–24882.
35 Shankar et al. *Met Clin Exp* 1998; 47:573–577.
36 Balkan and Dunning. *Diabetes* 1994;43:1173–1179.
37 Zawalich and Zawalich. *Endocrinology* 1992; 130:3135–3142.
38 Traxinger and Marshall. *J. Biol. Chem.* 1992; 267, 9718–9723.
39 Marshall et al. *J. Biol. Chem.* 1991; 266, 10155–10161.
40 Traxinger and Marshall, *J. Biol. Chem.* 1991; 266, 10148–10154.
41 Marshall et al. *J. Biol. Chem.* 1991; 266, 4706–4712.
42 Virkamaki et al. *Endocrinology* 1997; 138, 2501–2507.
43 McClain and Crook. *Diabetes* 1996; 45, 1003–1009.
44 Rossetti et al. *J. Clin. Investig.* 1995; 96, 132–140.
45 Hawkins et al. *J. Clin. Investig.* 1997; 99, 2173–2182.
46 Hresko et al. *J. Biol. Chem.* 1998; 273, 20568–20668.

Any patents or publications mentioned in this specification are indicative of the levels of those skilled in the art to which the invention pertains. These patents and publications are herein incorporated by reference to the same extent as if each individual publication was specifically and individually indicated t o be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of protecting isolated pancreatic islet β-cells from toxicity of nitric oxide and/or streptozotocin-like molecules that are generated during isolation, wherein said method comprises the steps of:

excising said islet β-cells from a freshly resected pancreas;

resuspending said islets in an isolation buffer containing one or more compounds that metabolically stimulate the glucosamine pathway, wherein said compounds are selected from the group consisting of glucosamine, N-acetylglucosamine, a combination of glutamine and glucose, and high concentration glucose, wherein high concentration glucose is defined as at least 6 mM glucose; and, maintaining said islet β-cells in solutions containing one or more of said compounds that stimulate the glucosamine pathway throughout subsequent isolation steps.

2. The method in claim 1, wherein said compounds are glucose in a concentration range of from about 6 mM to about 300 mM and glutamine in a concentration range of from about 0.001 mM to about 300 mM.

3. The method in claim 1, wherein said compound is glucosamine in a concentration range of from about 0.001 mM to about 300 mM.

4. The method in claim 1, wherein said compound is N-acetylglucosamine in a concentration range of from about 0.001 mM to about 300 mM.

* * * * *

UNITED STATES PATENT AND TRADEMARK OFFICE
CERTIFICATE OF CORRECTION

PATENT NO.     : 6,361,995 B1
DATED          : March 26, 2002
INVENTOR(S)    : Robert Konrad and Jeffrey Kudlow It is certified that error appears in the above-identified patent and that said Letters Patent is hereby corrected as shown below:

<u>Title page,</u>
Item [73], Assignee, "NAB Research Foundation" should read -- UAB Research Foundation --.

Signed and Sealed this

Eighteenth Day of February, 2003

JAMES E. ROGAN
*Director of the United States Patent and Trademark Office*